United States Patent
Kelley

(10) Patent No.: US 10,052,112 B1
(45) Date of Patent: Aug. 21, 2018

(54) METHODS AND SYSTEMS FOR REAMING THE FEMORAL CANAL

(71) Applicant: Scott Kelley, Chapel Hill, NC (US)

(72) Inventor: Scott Kelley, Chapel Hill, NC (US)

( * ) Notice: Subject to any disclaimer, the term of this patent is extended or adjusted under 35 U.S.C. 154(b) by 977 days.

(21) Appl. No.: 14/330,660

(22) Filed: Jul. 14, 2014

Related U.S. Application Data

(60) Provisional application No. 61/846,393, filed on Jul. 15, 2013.

(51) Int. Cl.
*A61B 17/00* (2006.01)
*A61B 17/16* (2006.01)
*A61B 17/17* (2006.01)

(52) U.S. Cl.
CPC ........ *A61B 17/1668* (2013.01); *A61B 17/175* (2013.01)

(58) Field of Classification Search
CPC ............ A61B 17/1659; A61B 17/1668; A61B 17/175
USPC .................................................... 606/79–85
See application file for complete search history.

(56) References Cited

U.S. PATENT DOCUMENTS

| | | | |
|---|---|---|---|
| 5,843,123 A | 12/1998 | Brazeau | |
| 6,517,581 B2 * | 2/2003 | Blamey | A61B 17/164 606/172 |
| 7,004,972 B2 | 2/2006 | Yoon | |
| 2004/0236341 A1 | 11/2004 | Petersen | |
| 2007/0100334 A1 * | 5/2007 | McFarlin | A61B 17/1622 606/45 |
| 2011/0046745 A1 | 2/2011 | Daniels et al. | |
| 2011/0112540 A1 | 5/2011 | McLean et al. | |
| 2014/0128987 A1 | 5/2014 | Kelley | |

OTHER PUBLICATIONS

Callaghan et al., ed. The Adult Hip. vol. 2, 2nd ed. Chapter 60, pp. 884-910, and Chapter 70, pp. 1025-1035. 2007. Lippincott Williams & Wilkins, Philadephia, PA.
Hansen et al. "The Rottinger approach for total hip arthroplasty: technique and review of the literature" Curr Rev. Musculoskelet Med (2011) 4:132-138. Springer, Berlin, Germany.
"Zimmer Natural-Hip™ System Surgical Technique" Informational Booklet. 25 pages. 2005. Zimmer, Inc. Warsaw, IN.
"CPT® 12/14 Hip System. Surgical Technique for Primary Hip Arthroplasty" Informational Booklet. 27 pages. 2002. Zimmer, Inc. Warsaw, IN.
"Alloclassic® Hip System Surgical Technique" Informational Booklet. 20 pages. 2003. Zimmer, Inc. Warsaw, IN.
"ZMR® Hip System" Informational literature, 20 pages. 2003. Zimmer, Inc. Warsaw, IN.
"Zimmer® M/L Taper Hip Prosthesis. Surgical Technique" Informational Booklet. 16 pages. 2010. Zimmer, Inc. Warsaw, IN.

(Continued)

*Primary Examiner* — Si Ming Ku
(74) *Attorney, Agent, or Firm* — Coats & Bennett, PLLC

(57) ABSTRACT

A tool and method of reaming one or more oblong cross-sectional sections of the femoral canal. The tool may include a reamer sized to be axially inserted into the canal and to be laterally pivoted within the canal. The tool may further include a guide to protect a proximal section of the femur. The guide also includes a channel through which the reamer is inserted to control an extent of movement of the reamer.

17 Claims, 6 Drawing Sheets

(56) References Cited

OTHER PUBLICATIONS

"Synergy Cemented Stem Surgical Technique" Informational Booklet, 31 pages. 2004. Smith & Nephew, Inc., Memphis, TN.
"Synergy Cementless Stem Surgical Technique" Informational Booklet, 32 pages. 2004. Smith & Nephew, Inc., Memphis, TN.
"ZMR Revision Taper Hip Prosthesis, Surgical Technique for Revision Hip Arthroplasty" 26 pages. 1999. Zimmer, Inc. Warsaw, IN.
"Summits® titanium tapered stem." Product description and illustration,1 page. 2001. DePuy Orthopaedics, Inc., Warsaw, IN.
Morrey, Bernard, ed. Joint Replacement Arthroplasty. Chapter 44, pp. 619-638. 1991. Churchill Livingstone, Inc., New York, NY.
"DePuy Revision Solutions. Hip Extraction Instrumentation Product Overview." 16 pages. 2009. DePuy Orthopaedics, Inc. Warsaw, IN.
"Moreland Cementless Hip Revision Instrumentation." Product Overview. 12 pages. 1998. DePuy Orthopaedics, Inc. Warsaw, IN.
Digioia, A.M., et al., "HipNav: Pre-operative Planning and Intra-operative Navigational Guidance for Acetabular Implant Placement in Total Hip Replacement Surgery." Proc. of the Computer Assisted Orthopaedic Surgery Symposium, Bern, Switzerland, Nov. 1995.

* cited by examiner

METHODS AND SYSTEMS FOR REAMING THE FEMORAL CANAL

CROSS-REFERENCE TO RELATED APPLICATIONS

The present application claims the benefit of U.S. Application No. 61/846,393 filed on Jul. 15, 2013, and entitled Methods and Systems for Reaming the Femoral Canal. This application is hereby incorporated by reference in its entirety.

FIELD OF THE INVENTION

The present application is directed to a methods and tools for reaming the femoral canal and, more particularly, to forming a non-circular sectional shape to accommodate a femoral component for use in a hip replacement procedure.

BACKGROUND

Hip replacement procedures involve the replacement of the hip joint formed by the head of the femur and the acetabulum of the pelvic bone. Hip replacement procedures include the preparation of the femur for receipt of a first femoral component and preparation of the acetabulum to receive a second acetabular component. The two components engage together to replace the hip joint. Numerous surgical approaches exist exposing the joint to perform hip replacement surgeries.

The preparation of the femur includes shaping the femoral canal to receive the femoral component. This may include reaming the canal using one or more reamers. The reamers are inserted into the canal and axially moved along the canal length.

Existing reaming techniques may damage the proximal femur during the axial movement of the reamer. Additionally, the reaming may not properly shape the femoral canal to receive the femoral component.

SUMMARY

The present application is focused on controlling rotation of a femoral component within the reamed femoral canal. The methods include introducing a slight oblong cross-section to the canal. In one embodiment, the design would add another 1-3 degrees of taper to the medial and lateral implant borders.

Tapered implants ideally rely on line-to-line reamers matching the exact stem taper, preventing subsidence of the femoral component. The ability to create a different taper in two different planes may involve the use of modifications to current reaming systems, both proximally and distally. Distally, the modification would involve a sphere or other design that provides a fulcrum around which the reamer could pivot on, in a defined controlled plane. Proximally, a reamer guide would control the direction and limits of the reamer as it pivots on the distal portion of the reamer, such as on the sphere located at the distal end.

The present application is directed to methods of forming an oblong cross-sectional shape along one or more regions of the femoral canal. This oblong shape provides for receiving a femoral component with a stem having an oblong shape.

One embodiment is directed to a method of reaming the femoral canal that includes inserting a reamer in an axial direction into the femoral canal. The method also includes reaming at least one region of the femoral canal while inserting the reamer in the axial direction and forming a circular cross-sectional shape along the at least one region. The method also includes pivoting the reamer laterally within the femoral canal and forming an oblong cross-sectional shape along the at least one region.

Pivoting the reamer laterally may include pivoting the reamer about a spherical member positioned at a distal end of the reamer.

The method may also include inserting the reamer through a channel in a guide and pivoting the reamer laterally until the reamer contacts against an edge of the channel.

The method may include reaming an intermediate region and a proximal region of the canal to have an oblong cross-sectional shape with a distal region of the canal having a circular cross sectional shape.

Another embodiment is directed to a method of reaming the femoral canal that includes positioning a guide at a proximal end of the femur and aligning a channel in the guide with the femoral canal. The method includes inserting a reamer in an axial direction through the channel and into the femoral canal and forming a circular cross-sectional shape along a region of the canal. While the reamer is inserted in the canal, pivoting the reamer about a distal end in opposing first and second directions and reaming the region of the canal and forming an oblong cross-sectional shape along the region of the canal. The method also includes moving the reamer along the axial direction and removing the reamer from the femoral canal and the channel in the guide.

The channel in the guide may include an oblong shape and pivoting the reamer in opposing first and second directions may include moving the reamer along a major axis of the channel. This may further include limiting an extent of pivoting movement in the first direction by contacting the reamer against a first edge of the channel which is located along the major axis and limiting an extent of the pivoting movement in the second direction by contacting the reamer against a second edge of the channel which is located along the major axis.

One embodiment is directed to a tool to ream the femoral canal of a femur. The tool includes a guide configured to be positioned at the proximal end of the femur. The guide includes a body with a first side shaped to conform to the proximal end of the femur and an opposing second side, and a channel that extends through the body from the first side to the second side with the channel including an elongated shape in a plane perpendicular to a centerline of the channel with a major axis that includes a length and a minor axis that includes a width. The tool also includes an elongated reamer that extends through the guide. The reamer includes a shaft section that is positioned in the channel and includes a cross-sectional size with a width that is substantially the same as the width of the channel and a length that is smaller than the length of the channel. The relative sizes in the lengths and the widths of the channel and the shaft provide for movement of the shaft along the length of the channel and prevent movement of the shaft along the width of the channel. The reamer also includes a cutting section positioned distally from the shaft and outward beyond the first side of the body of the guide with the cutting section including one or more teeth shaped to ream the femur. The reamer also includes a rounded tip positioned at a distal end of the reamer.

The rounded tip of the reamer may include a spherical shape. The rounded tip may also be a separate piece from a remainder of the reamer.

The width of the channel may be constant along a majority of the length.

The shaft may include a circular cross-sectional shape and ends of the channel along the major axis may include a curved shape.

The tool may also include a flange positioned along the shaft section of the reamer and the flange may be larger than the channel to prevent insertion of the flange into the channel.

The cutting section may be tapered and may reduce in size towards the distal end of the reamer.

The channel may be contained within the body and may include a continuous outer wall.

Another embodiment is directed to a tool to ream the femoral canal of a femur. The tool includes a guide configured to be positioned at the proximal end of the femur. The guide includes a body and a channel that extends through the body. The channel includes an elongated shape in a plane perpendicular to a centerline of the channel with a length and a smaller width with the width being constant along a majority of the channel. The channel is contained within the body and includes a continuous outer wall. The tool also includes a reamer that extends through the guide. The reamer includes a first section that extends through the body, and a second section located distally from the first section and that terminates at a rounded distal tip. The second section extends outward beyond the body of the guide. The first section includes a circular cross-sectional shape with a diameter that is that is substantially equal to the width of the channel and smaller than the length of the channel to move along the length of the channel during pivoting movement of the reamer about the rounded distal tip and to prevent movement across the width of the channel. The second section includes one or more teeth to cut the femur during the pivoting movement of the reamer about the rounded distal tip.

The reamer may also include a third section located proximally from the first section with the third section extending outward beyond the body of the guide in a direction opposite from the second section.

The rounded distal tip may include a spherical shape with a smooth exterior surface.

The second section may include a tapered shape that narrows towards the rounded distal tip.

The one or more teeth of the second section may be axially spaced away from the rounded distal tip.

The first section of the reamer may include a smooth exterior surface.

Another embodiment is directed to a tool to ream the femoral canal of a femur. The tool includes an elongated reamer with a proximal shaft, a cutting section located distally of the shaft, and a rounded distal tip. The tool also includes a guide with a body that includes a channel that extends through the body from a first side to a second side. The channel is contained within the body and includes a continuous outer wall. The channel also includes an oblong shape in a plane perpendicular to a centerline of the channel with a length that is greater than the width. The reamer extends through the guide with the proximal shaft extending through the body. The cutting section is positioned outward beyond the first side of the body. The cutting section is movable along the length of the channel to move the cutting section within a lateral plane during pivoting movement of the reamer about the rounded distal tip. The cutting section is sized relative to the width of the channel to prevent movement out of the lateral plane.

The proximal shaft may include a width substantially the same as the channel to prevent the movement out of the lateral plane.

The proximal shaft may include a circular cross-sectional shape.

The width of the channel may be constant along a majority of the length.

The rounded distal tip may include a spherical shape with a smooth exterior surface.

The cutting section may be axially spaced away from the rounded distal tip along the reamer.

These various aspects may be used together in a single procedure. Alternatively, the various aspects may be used separately.

DETAILED DESCRIPTION

The present application is directed to tools and methods of reaming one or more oblong cross-sectional sections of the femoral canal. The tools include a reamer sized to be axially inserted into the canal and to be laterally pivoted within the canal. The tool may further include a guide to protect a proximal section of the femur and to control an extent of movement of the reamer.

Figure 1:
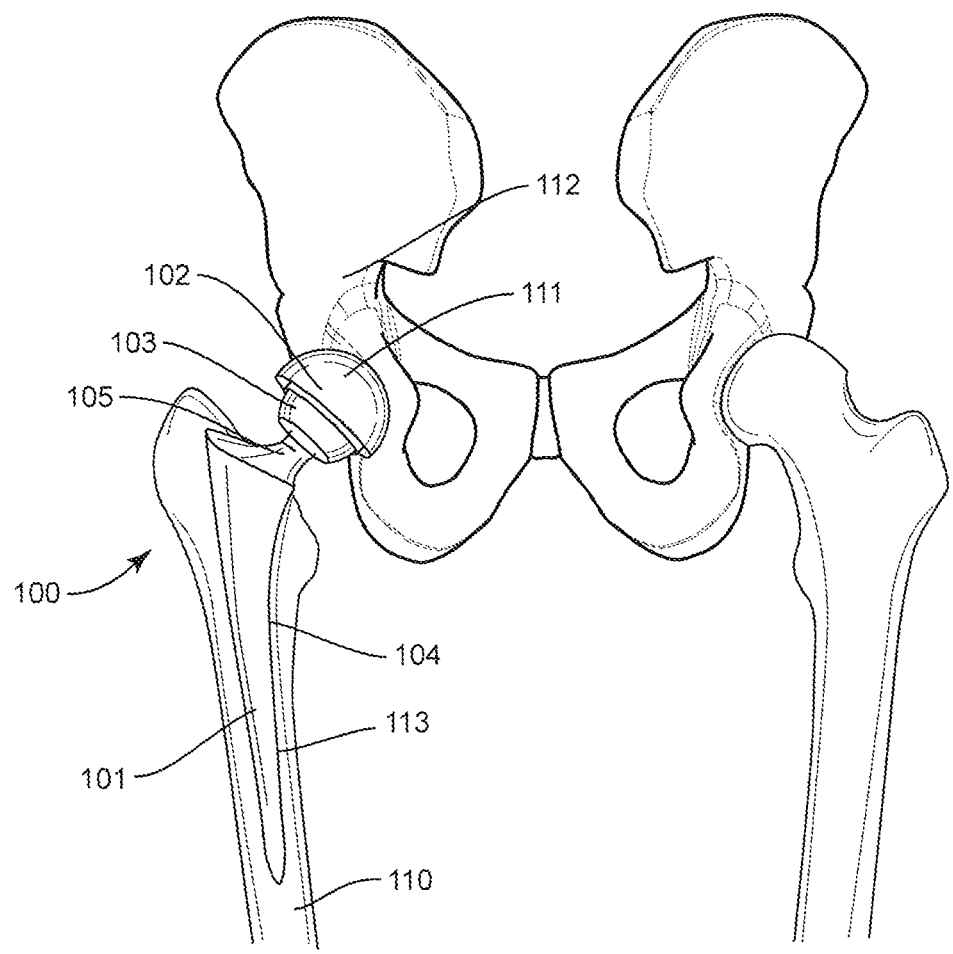
FIG. 1 is a schematic view of a hip replacement implant including a femoral component and an acetabular component implanted within a patient.

FIG. 1 illustrates a hip replacement implant 100 positioned within a patient. The implant 100 includes a femoral component 101 that is attached to the femur 110, and an acetabular component 102 that is attached to the acetabulum 111 in the pelvic bone 112. The femoral component 101 includes a head 103 that seats within a receptacle of the acetabular component 102. This replacement joint replicates the hip joint and provides for pivoting movement of the femur 110 relative to the pelvic bone 112.

The femoral component 101 generally includes a stem 104, a neck 105 that extends medially inward after implanted in the patient and that terminates at a mount, and the head 103 that attaches to the mount. The stem 104 is sized to fit into the interior of the femur 110, and particularly into the femoral medullary canal 113 (hereinafter referred to as the femoral canal or canal 113). The exterior surface of the stem 104 may include one or more surfaces configured to encourage bonding by allowing the bone to grow into and/or onto the surface of the stem. This provides for the femoral component 101 to become integrated with the femur 110 thus reducing the likelihood of loosening.

Figure 2A:
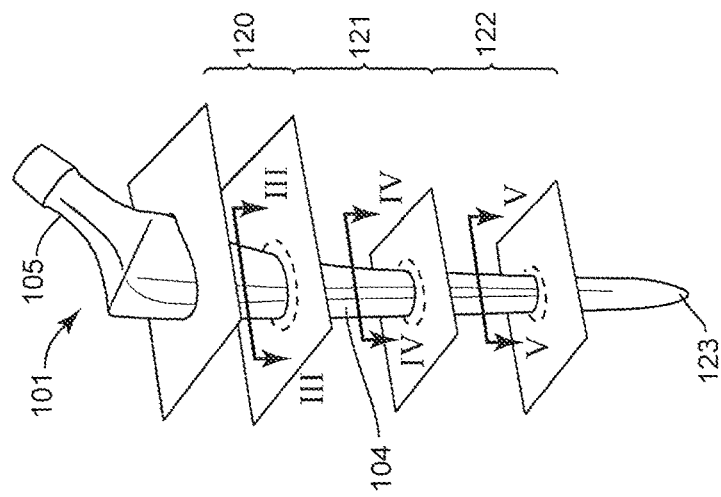
FIG. 2A is a perspective view of a femoral component with a stem having a circular cross-sectional shape along its length.

FIG. 2A illustrates an embodiment of a femoral component 101 with a stem 104 having a proximal section 120, an intermediate section 121, and a distal section 122. The stem 104 terminates at a tip 123. The stem 104 includes a varying size along its length that tapers from the proximal section 120 to the distal section 122 to generally match the anatomy of the femur 110 and to provide secure fixation within the canal 113. This femoral component 101 includes a circular cross-sectional shape throughout a majority of the stem 104. The circular cross-sectional shape extends along the proximal 120, intermediate 121, and distal sections 122. FIG. 2A includes dashed lines illustrating the circular cross-sectional shapes of the stem 104 at the various sections along the length. The stem 104 reduces in size along the length with the proximal section 120 including a greater cross-sectional area than the distal section 122.

The methods and devices for this procedure apply to a variety of different reamer-based systems. These include systems that use various sizes and shapes of tapered femoral components 101, as well as femoral components 101 having straight stems. In one embodiment, the best results are obtained using a tapered implant, as opposed to a straight stem implant. In specific embodiments, the implant includes a 3° taper.

Preparation of the femoral canal 113 to receive this component 101 includes axial reaming of the femoral canal 113 that shapes the canal into a circular cross-sectional shape. This circular shape may occur by axial insertion and removal of a reamer into and out of the femoral canal 113. A drawback of this type of femoral component 101 is the occurrence of rotation within the femoral canal 113. The rotation may occur due to the circular cross-sectional shapes of both the stem 104 and canal 113.

Figure 2B:
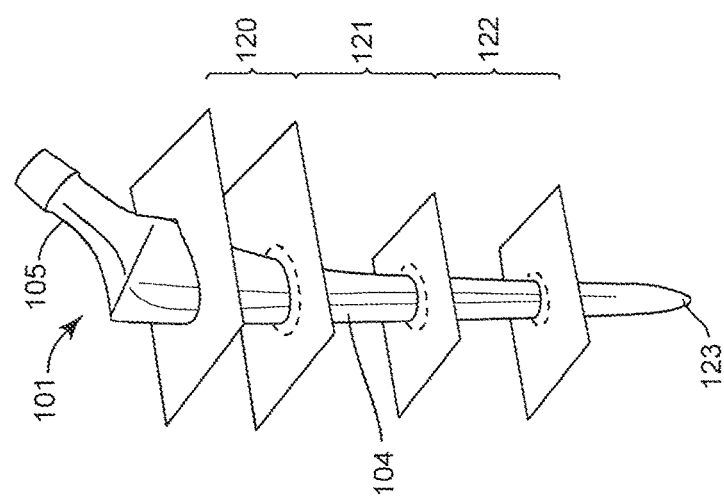
FIG. 2B is a perspective view of a femoral component with a stem having an oblong cross-sectional shape along its length
Figure 3:
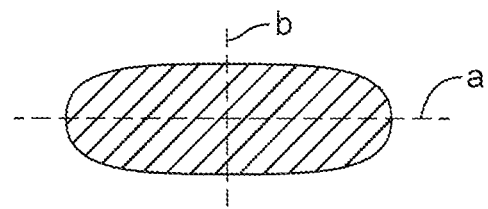
FIG. 3 is a section view cut along line III-III of FIG. 2B.
Figure 4:
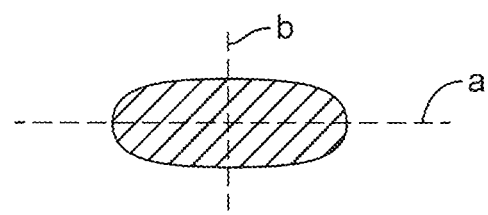
FIG. 4 is a section view cut along line IV-IV of FIG. 2B.
Figure 5:
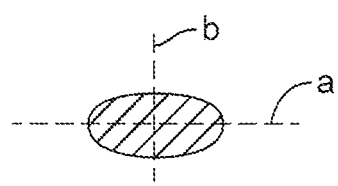
FIG. 5 is a section view cut along line V-V of FIG. 2B.

FIG. 2B includes a femoral component 101 applicable to the oblong reaming method. The component 101 includes a stem 104 with an oblong cross-sectional shape along the proximal 120, intermediate 121, and distal 122 sections. The dashed lines in FIG. 2B illustrate the oblong cross-sectional shapes along the length. FIG. 3 illustrates a cross-sectional view of the stem 104 along the proximal section 120. FIG. 4 includes a cross-sectional shape along the intermediate section 121. FIG. 5 includes a cross-sectional shape along the distal section 122. As illustrated in these Figures, as well as the dashed lines in FIG. 2B, the stem 104 includes an oblong cross-sectional shape along these sections of the stem 104. Each oblong shape includes a major axis a and a minor axis b. The section adjacent to the tip 123 includes a circular cross-sectional shape. An advantage of this oblong design is to prevent rotation of the femoral component 101 within the femoral canal 113. However, the femoral canal 113 should be sized to accommodate the oblong shape of the stem 104.

FIG. 2B includes the stem 104 having an oblong cross-sectional shape along the length of the stem 104 until substantially reaching the tip 123. Other applicable embodiments may include the shape tapering to a circular cross-section at a more proximal location along the length. In one embodiment, the shape tapers to a circular shape between the intermediate and distal sections 121, 122.

Techniques disclosed in the present application include sizing of the femoral canal 113 to receive the femoral component 101 with an oblong cross-sectional shape. This sizing accommodates the non-circular cross-sectional shape of the intermediate section 121. This technique may also be used to size additional regions of the canal 113 (e.g., the proximal and distal regions).

In this embodiment, sizing of the femoral canal 113 occurs initially at the distal and proximal regions that accommodate respectively the proximal section 120 and distal section 122 of the femoral component 101. U.S. patent application Ser. No. 13/671,357 filed on Nov. 7, 2012 and titled "Methods and Devices for a Surgical Hip Replacement Procedure" and published as US Patent Publication No. 2014/0128987, discloses aspects of reaming the femoral canal and is herein incorporated by reference in its entirety. Sizing of an intermediate portion 121 of the femoral canal 113 that accommodates the intermediate section 121 is then subsequently performed.

Figure 6:
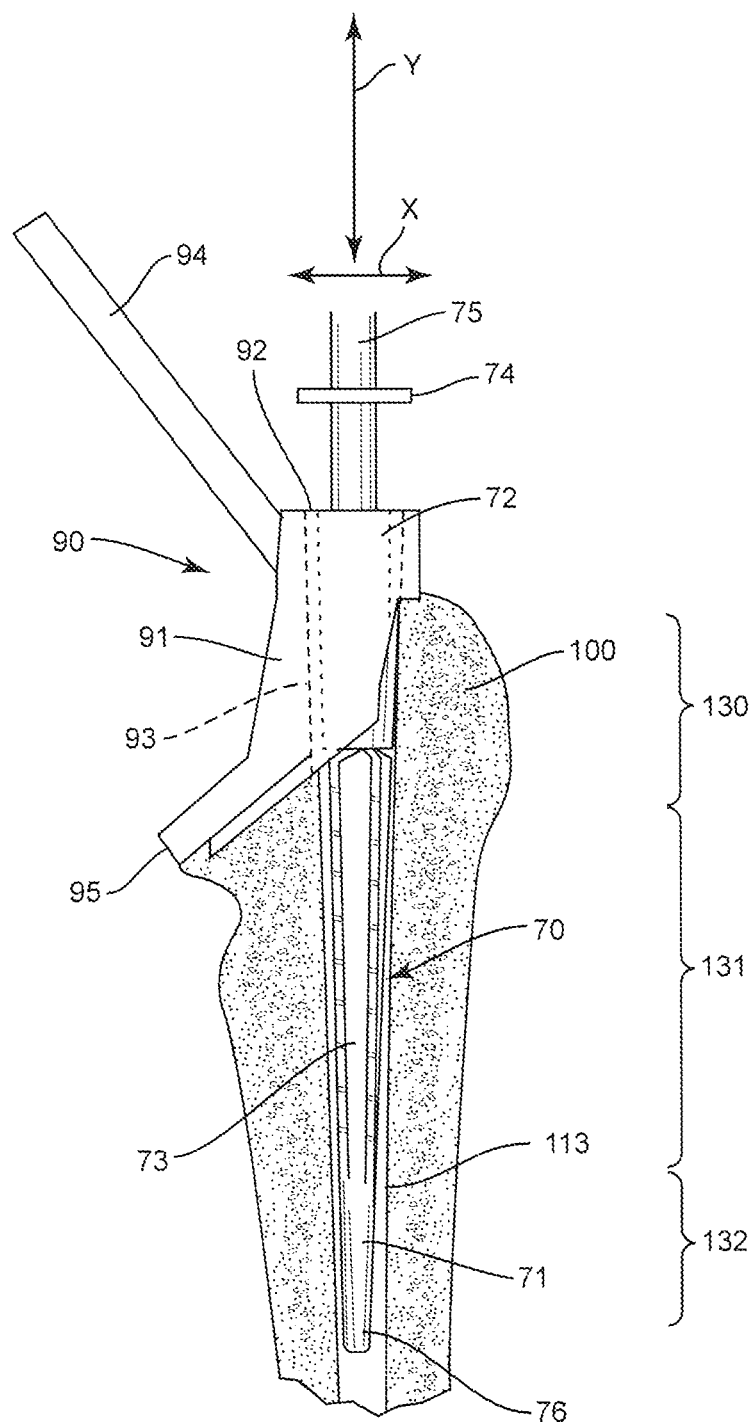
FIG. 6 is a cut-away side schematic view of a reamer within the femoral canal.

FIG. 6 illustrates one embodiment of reaming the intermediate region 131 of the femoral canal 113 to accommodate the component 101. In the embodiment of FIG. 6, the femoral canal 113 has already been reamed along distal 132 and proximal 130 regions. Reaming of the intermediate region 131 of the femoral canal 113 is performed using a mid-shaft reamer 70 and a guide 90.

The mid-shaft reamer 70 is inserted into the canal 113 for reaming the intermediate region 131 that has not previously been prepared by distal or proximal reamers. The mid-shaft reamer 70 includes an elongated shape with a distal section 71 that aligns with the previously-reamed distal region 132, and a proximal section 72 that aligns with the previously-reamed proximal region 130. The sections 71, 72 of the reamer 70 may each include a smooth exterior surface.

A cutting section 73 is positioned along an intermediate length of the reamer 70 between sections 71, 72. In the embodiment of FIG. 6, the cutting section 73 includes a tapered shape. The tapering shape may coincide with a tapered shape of the intermediate section 121 of the stem 104. The cutting section 73 may include a set of parallel straight or helical cutting edges. The edges may be orientated at an angle and include an underneath undercut. Helical edges may be aligned in either clockwise or counter-clockwise spirals. A shaft 75 extends axially outward in a proximal direction from the proximal section 72. The shaft 75 may include a smooth exterior surface and a circular cross-sectional shape to prevent damage in the event of contact with the nearby tissue.

The depth of reaming of the middle region of the canal 113 may be controlled in various manners. A flange 74 is positioned along the shaft 75 and includes a greater width than the shaft 75. The flange 74 functions as a depth stop and contacts against a control surface, such as the top surface of the guide 90, to control an extent of reaming of the femoral canal 103. The flange 74 may be adjustable along the length of the shaft 75 to accommodate variations in the desired reaming levels. The insertion depth of the mid-shaft reamer 70 may also be controlled by the size of the distal section 71. The size of the distal section 71 causes engagement with the reamed distal region 132 and prevents further insertion into the femoral canal 113.

The mid-shaft reamer 70 may be used with a soft-tissue reamer guide 90 to protect the femur 100 and control a depth of reaming of the canal 103. The guide 90 includes a body 91 with a channel 93 to allow for passage of the mid-shaft reamer 70. The channel 93 is wider than the proximal section 72 of the reamer 70 to provide for pivoting movement as will be explained in detail below. A contact surface 92 is positioned on an outer side of the body 91 in proximity to the channel 93. An arm 94 may extend outward from the body 91 to allow for the placement and manipulation of the guide 90 by the surgeon. The guide 90 also includes an angled flange 95 that contacts against the femur 110.

In use, the guide 90 is placed at the proximal end of the femur 100 with the channel 93 being aligned with the femoral canal 113. The surgeon then inserts the reamer 70 through the channel 93 and into the canal 103 to ream the intermediate region 131. The body 91 protects the proximal end of the femur 100 from being directly contacted by the reamer 70 or a device driving the reamer 70, either of which could potentially damage the femur 100.

The reamer 70 is passed through the canal 113 in an axial up-and-down motion as illustrated by arrow Y to ream the intermediate region 131. Preferably, the reaming is performed in a single pass to prevent or eliminate damage to the surrounding tissue. This axial movement and reaming forms a circular cross-sectional shape along the intermediate region 131 of the canal 113. This shape may not facilitate the oblong cross-sectional shape of the intermediate section 121 of the stem 104. Therefore, the components are further configured for lateral movement of the reamer 70 relative to the femur 110.

To ream the canal 113 to form an oblong cross-sectional shape, the reamer 70 is also moved within a plane laterally in a back-and forth motion. As illustrated in FIG. 6, the movement is illustrated by arrow X. The proximal section 72 of the reamer 70 includes a smaller width than the channel 93 of the guide 90. As illustrated, gaps are positioned between the inner edges of the channel 93 and the proximal section 72. This difference in sizing provides for the reamer 70 to be moved laterally within a plane to ream the oblong cross-sectional shape along the intermediate section of the canal 113. Further, the extent of the movement is controlled based on the size of the gaps. The reamer 70 is prevented from being moved beyond an angular position in which the proximal section 72 of the reamer 70 contacts against the inner edges of the channel 93.

The amount of reaming may vary depending upon the patient. In one embodiment, the design adds another 1-3 degrees of taper to the medial and lateral implant borders.

Figure 7:
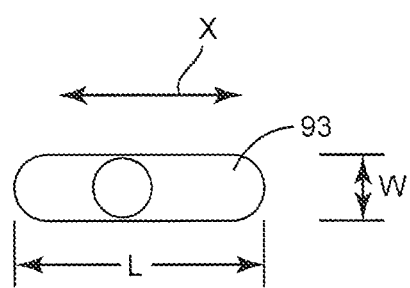
FIG. 7 is a schematic view of a reamer positioned within a channel of a guide.

The movement of the reamer 70 may be isolated to just the axial and lateral planes during the reaming process. In this configuration, the reamer 70 is fully axially inserted into the femoral canal 113 prior to any lateral movement. This may include insertion of the reamer 70 into the canal 113 until the flange 74 contacts against the contact surface 92 of the guide 90. FIG. 7 illustrates one embodiment that controls the movement of the reamer 70. The channel 93 includes an elongated shape with a greater length L than the proximal section 72. The channel 93 also includes a width W that is substantially the same as the section 72. This relative sizing allows for movement of the shaft 75 just within the plane along the length L of the channel 93. As illustrated, the channel 93 is aligned such that the length L is aligned with the desired direction of the lateral reamer movement indicated by arrow X. The extent of movement along the length of the channel 93 is controlled by the relative differences in the lengths. The relative sizes of the widths W prevents or reduces movement out of the plane.

The cutting section 73 of the reamer 70 may also extend into one or both of the proximal 130 and distal 132 regions of the canal 113. The lateral movement of the reamer 70 therefore also causes additional reaming of one or both of these regions 130. This results in the application region(s) also having an oblong shape to accommodate the femoral component 101.

In other embodiments, the reaming may include a combination of simultaneous axial and lateral movement of the reamer 70 within the canal 113 to form the oblong cross-sectional shape along the intermediate section 121. The reamer 70 may be axially and laterally moved during the reaming process to simultaneously ream the canal 113 along multiple planes.

The distal section 71 of the reamer 70 is also configured to accommodate the lateral movement within the canal 113. In one embodiment as illustrated in FIG. 6, the distal section 71 includes a narrower width than the distal region of the canal 113. This smaller size allows for pivoting movement of the reamer 70 during the process.

Figure 8:
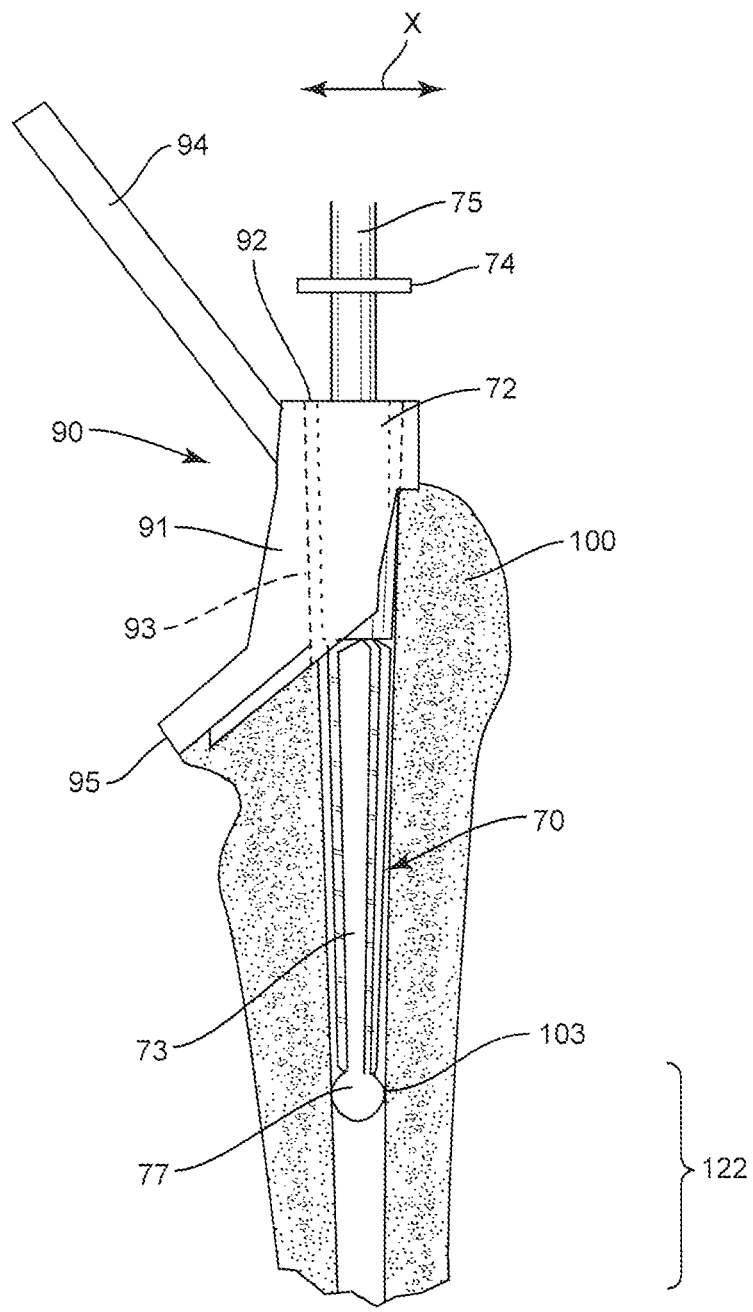
FIG. 8 is a cut-away side schematic view of a reamer within the femoral canal.

FIG. 8 discloses another embodiment with the reamer 70 including a spherical distal end 77. The spherical end 77 may be adjacent to the cutting section 73 as illustrated, or may be spaced axially away by a non-cutting distal section (not illustrated). The spherical end 77 may include a smooth surface to facilitate the pivoting movement of the reamer 70. The spherical end 77 is sized to fit within the distal region 132 of the canal 113 and is sized to provide for pivoting movement of the reamer 70 about the end 77.

In one embodiment, the spherical end 77 may be a separate element that is attached to the distal end of the reamer 70. In this embodiment, the reamer 70 may be initially axially inserted into the canal 113 to ream the intermediate section 121. This reaming forms a circular cross-sectional shape along the intermediate section 121 of the canal 113. The reamer 70 is then removed from the canal 113 and the spherical end 77 is attached. The reamer 70 is then inserted axially back into the canal 113. Once inserted, the reamer 70 is pivoted to form the oblong cross-sectional shape along the canal 113. In another embodiment, the end 77 is fixedly connected with the reamer 70.

The procedure provides for creating a taper in the canal 113 along two different planes. A first plane occurs during axial movement of the reamer 70 along the length (i.e. depth) of the canal 113. A second plane occurs during lateral movement of the reamer 70. In one embodiment, the reaming in the second plane occurs as the reamer 70 pivots about the distal section of the reamer, with one particular embodiment featuring the pivoting movement occurring about the spherical end 77. Proximally, the extent of the reaming is controlled by the size of the channel 93 in the guide 90. The channel 93 controls the direction and limits of the reamer 70 as it pivots about the distal end.

The reaming of the intermediate region may be accomplished by a single reamer, or a series of graduated reamers. The reamers include graduated sizes with each having an increasing diameter cutting section. The reamers 70 are inserted into the femoral canal 103 in order with each subsequent reamer 70 being larger than the previous reamer.

This process may further be used with reamers 70 having cutting sections 73 along other sections of the length to create different cross-sectional shapes on the proximal and/or distal regions. These processes include a similar operation in which a reamer with a cutting portion is inserted axially to the applicable depth along the canal 113. The reamer is further moved laterally within the canal 113 to ream the oblong cross sectional shape.

The process described above includes initially sizing of the canal 113 at distal 132 and proximal regions 130, and then subsequently sizing the intermediate region 131. The process may also be performed in other sequences. In one embodiment, the entire canal 113 is initially sized, followed by additional reaming of one or more regions by one or more separate reamers. This additional reaming forms one or more regions with an oblong cross-sectional shape.

The various methods and systems may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

The invention claimed is:

1. A tool to ream the femoral canal of a femur, the tool comprising:
   a guide configured to be positioned at a proximal end of the femur, the guide comprising:
      a body with a first side shaped to conform to the proximal end of the femur and configured to contact the femur, an opposing second side, and a continuous outer wall that extends between the first and second sides;
      a channel that extends entirely through the body from the first side to the second side and is contained within the outer wall, the channel includes a centerline and an elongated shape in a plane perpendicular to the centerline with a major axis that includes a length and a minor axis that includes a width;
   an elongated reamer that extends through the guide, the reamer comprising:
      a shaft that extends through the channel and includes a cross-sectional size with a width that is substantially the same as the width of the channel and a length that is smaller than the length of the channel, the relative sizes in the lengths and the widths of the channel and the shaft provide for movement of the shaft along the length of the channel and prevent movement of the shaft along the width of the channel;
      a cutting section positioned distally from the shaft and outward beyond the first side of the body of the guide, the cutting section including one or more teeth shaped to ream the femur; and
      a spherical tip positioned at a distal end of the reamer, the spherical tip configured to allow pivoting of the reamer relative to the guide for movement of the shaft along the length of the channel;
      the shape of the reamer and the guide are configured for the reamer to move just laterally back and forth along the channel while the spherical tip remains at an axial position along the femoral canal to ream an oblong cross-sectional shape in the femoral canal.

2. The tool of claim 1, wherein the spherical tip is a separate piece from a remainder of the reamer.

3. The tool of claim 1, wherein the width of the channel is constant along a majority of the length.

4. The tool of claim 1, wherein the shaft includes a circular cross-sectional shape and the channel includes opposing ends positioned along the major axis that include a curved shape.

5. The tool of claim 1, further comprising a flange positioned along the shaft of the reamer, the flange being larger than the channel to prevent insertion of the flange into the channel.

6. The tool of claim 1, wherein the cutting section is tapered and reduces in size towards the distal end of the reamer.

7. A tool to ream the femoral canal of a femur, the tool comprising:
   a guide configured to be positioned at a proximal end of the femur, the guide comprising:
      a body with a first side configured to contact against the femur and an opposing second side, and an outer wall that extends between the first and second sides;
      a channel that extends entirely through the body from the first side to the second side and is contained within the outer wall, the channel includes an elongated shape in a plane perpendicular to a centerline of the channel with a length and a smaller width, the width being constant along a majority of the channel, the channel being contained within the body and including a continuous outer wall;
   a reamer that extends through the guide, the reamer comprising:
      a first section that extends through the body; and
      a second section located distally from the first section and terminates at a spherical distal tip, the second section extending outward beyond the body of the guide;
      the first section including a circular cross-sectional shape with a diameter that is substantially equal to the width of the channel and smaller than the length of the channel to move along the length of the channel during pivoting movement of the reamer about the spherical distal tip and to prevent movement across the width of the channel;
      the second section including one or more teeth to cut the femur during the pivoting movement of the reamer about the spherical distal tip;
      the reamer and guide being shaped for movement of the reamer back and forth just within the plane perpendicular to the centerline for the first section to ream an oblong shape in the femoral canal during pivoting movement of the reamer about the spherical distal tip.

8. The tool of claim 7, further comprising a third section of the reamer located proximally from the first section, the third section extending outward beyond the body of the guide in a direction opposite from the second section.

9. The tool of claim 7, wherein the second section includes a tapered shape that narrows towards the spherical distal tip.

10. The tool of claim 7, wherein the one or more teeth of the second section are axially spaced away from the spherical distal tip.

11. The tool of claim 7, wherein the first section of the reamer includes a non-textured exterior surface.

12. A tool to ream a femoral canal of a femur, the tool comprising:

an elongated reamer with a proximal shaft, a cutting section located distally of the shaft, and a spherical distal tip;

a guide with a body that includes a channel that extends entirely through the body from a first side configured to contact against the femur to a second side opposite from the first side, the guide also including a lateral wall that extends between the first and second sides, the channel being contained within the body and including a continuous outer wall, the channel including an oblong shape in a plane perpendicular to a centerline of the channel with a length that is greater than the width;

the reamer extending through the guide with the proximal shaft extending through the body, the cutting section positioned outward beyond the first side of the body;

the proximal shaft being movable along the length of the channel to move the cutting section within a lateral plane during pivoting movement of the reamer about the spherical distal tip and with the spherical distal tip remaining axially stationary along a longitudinal axis of the femoral canal during the pivoting movement;

the proximal shaft being sized relative to the width of the channel to prevent movement out of the lateral plane.

13. The tool of claim 12, wherein the proximal shaft includes a width substantially the same as the channel to prevent the movement out of the lateral plane.

14. The tool of claim 12, wherein the proximal shaft includes a circular cross-sectional shape.

15. The tool of claim 12, wherein the width of the channel is constant along a majority of the length.

16. The tool of claim 12, wherein the distal tip includes a non-textured exterior surface.

17. The tool of claim 12, wherein the cutting section is axially spaced away from the distal tip along the reamer.

* * * * *